United States Patent
Wang et al.

(10) Patent No.: US 9,847,543 B2
(45) Date of Patent: Dec. 19, 2017

(54) FUEL CELL SYSTEM HAVING BIOGAS DESULFURIZER ASSEMBLY WITH MANGANESE OXIDE DESULFURIZER MATERIAL

(71) Applicant: FUELCELL ENERGY, INC., Danbury, CT (US)

(72) Inventors: Jin-Yun Wang, Cheshire, CT (US); Mohammad Farooque, Danbury, CT (US); David Xu, Medfield, MA (US); Zachary Sanders, Pardeeville, WI (US)

(73) Assignee: FUELCELL ENERGY, INC., Danbury, CT (US)

( * ) Notice: Subject to any disclaimer, the term of this patent is extended or adjusted under 35 U.S.C. 154(b) by 619 days.

(21) Appl. No.: 13/786,571

(22) Filed: Mar. 6, 2013

(65) Prior Publication Data
US 2014/0255805 A1    Sep. 11, 2014

(51) Int. Cl.
*H01M 8/0662*    (2016.01)
*H01M 8/04014*    (2016.01)
*B01J 43/00*    (2006.01)
*C12M 1/00*    (2006.01)
(Continued)

(52) U.S. Cl.
CPC .......... *H01M 8/0675* (2013.01); *B01D 53/48* (2013.01); *B01D 53/8603* (2013.01); *B01J 43/00* (2013.01); *B01D 2251/602* (2013.01); *B01D 2253/1124* (2013.01); *B01D 2255/2073* (2013.01); *B01D 2255/20738* (2013.01); *B01D 2257/304* (2013.01); *B01D 2257/306* (2013.01); *B01D 2257/553* (2013.01); *B01D 2257/80* (2013.01); *B01D 2258/05* (2013.01); *C12M 47/18* (2013.01); *H01M 8/04014* (2013.01)

(58) Field of Classification Search
CPC .............................. H01M 8/0675; B01J 43/00
USPC ........................... 429/410; 423/700; 252/184
See application file for complete search history.

(56) References Cited

U.S. PATENT DOCUMENTS

| | | |
|---|---|---|
| 4,816,139 A | 3/1989 | Keyworth |
| 4,852,995 A | 8/1989 | Cordier et al. |
| 5,149,364 A | 9/1992 | Craig et al. |

(Continued)

FOREIGN PATENT DOCUMENTS

| | | |
|---|---|---|
| JP | H11-003723 | 1/1999 |
| JP | H11-350945 A | 12/1999 |

(Continued)

OTHER PUBLICATIONS

S. Velu et al., Regenerative Adsorbents for the Adsorptive Desulfurization of Transporation Fuels for Fuel Cell Applications, 226th ACS National Meeting, New York, NY, Sep. 7-11, 2003.

(Continued)

*Primary Examiner* — Sarah A Slifka
*Assistant Examiner* — Brian Ohara
(74) *Attorney, Agent, or Firm* — Foley & Lardner LLP (57) ABSTRACT

A desulfurizer material for desulfurizing fuel supplied to a fuel cell system, the desulfurizer material comprising one or more manganese oxide materials having an octahedral molecular sieve (OMS) structure, and the desulfurizer material being resistant to moisture and being capable of removing organic sulfur containing compounds and $H_2S$. The desulfurizer material is used in a desulfurizer assembly which is used as part of a fuel cell system.

16 Claims, 4 Drawing Sheets

(51) Int. Cl.
  *B01D 53/48* (2006.01)
  *B01D 53/86* (2006.01)

(56) References Cited

U.S. PATENT DOCUMENTS

| | | | | |
|---|---|---|---|---|
| 5,472,801 | A | * | 12/1995 | Mattejat ............... F28D 9/0031 429/508 |
| 5,478,662 | A | * | 12/1995 | Strasser ............. H01M 8/04119 429/414 |
| 5,846,406 | A | * | 12/1998 | Sudhakar ................ B01J 23/34 208/213 |
| 6,887,445 | B2 | | 5/2005 | Braga et al. |
| 6,979,505 | B2 | | 12/2005 | Grasso et al. |
| 7,063,732 | B2 | | 6/2006 | Katikaneni et al. |
| 7,374,666 | B2 | | 5/2008 | Wachs |
| 2002/0004155 | A1 | * | 1/2002 | Haltiner, Jr. ........ H01M 8/0228 429/434 |
| 2002/0071976 | A1 | * | 6/2002 | Edlund .................. B01D 53/02 422/600 |
| 2004/0129607 | A1 | | 7/2004 | Slater et al. |
| 2005/0022449 | A1 | * | 2/2005 | Katikaneni ........... B01D 53/48 48/198.3 |
| 2005/0169826 | A1 | | 8/2005 | Li et al. |
| 2006/0019130 | A1 | | 1/2006 | Katikaneni et al. |
| 2006/0177367 | A1 | * | 8/2006 | Li ........................ B01D 53/949 423/239.1 |
| 2008/0264254 | A1 | | 10/2008 | Song et al. |
| 2009/0065400 | A1 | | 3/2009 | Song et al. |
| 2009/0294353 | A1 | * | 12/2009 | Massie .................... C02F 1/463 210/601 |
| 2010/0135884 | A1 | | 6/2010 | Serban et al. |
| 2011/0247493 | A1 | * | 10/2011 | Hatscher ................ B01D 53/04 95/90 |
| 2012/0178005 | A1 | | 7/2012 | Kusnezoff et al. |
| 2013/0209338 | A1 | * | 8/2013 | Prasad ................... B01D 53/75 423/219 |

FOREIGN PATENT DOCUMENTS

| | | |
|---|---|---|
| JP | 2001-205004 | 7/2001 |
| JP | 2007-500265 A | 1/2007 |
| JP | 2007-527783 A | 10/2007 |
| JP | 2009-533829 | 9/2009 |
| JP | 2011-157987 A | 8/2011 |
| KR | 10-2009-0064716 | 6/2009 |
| WO | 03/095594 | 11/2003 |
| WO | 2012/006729 A1 | 1/2012 |
| WO | WO-2012/006729 A1 | 1/2012 |

OTHER PUBLICATIONS

S. Oh et al., Removal of Odorants by Selective Adsorption from Natural Gas for Protection of Steam Reforming Catalyst in Fuel Cell from Sulfur Poisoning, J. Korean Ind. Eng. Chem., vol. 18, No. 4, Aug. 2007.

S. Satokawa, Study on the adsorptive removal of organic sulfur compounds in city gas at ambient temperature using silver ion-exchanged zeolites, Journal of the Faculty of Science and Technology Seikei University, vol. 43, No. 2, pp. 11-14 (2006).

D. Shekhawat et al., Natural Gas Odorants Desulfurization, AIChE Annual National Meeting, Austin, TX, Nov. 7-12, 2004.

J. Lampert, "Selective catalytic oxidation: a new catalytic approach to the desulfurization of natural gas and liquid petroleum gas for fuel cell reformer applications." Journal of Power Sources (2004), 131(1-2), 27-34.

R.J. Spiegel, J.L. Preston. "Technical assessment of fuel cell operation on anaerobic digester gas at the Yonkers, NY, wastewater treatment plant." Waste Management (New York, NY) (2003) 23(8), 709-17.

Chuanteng He, Doug Herman, Ron G. Minet, Theodore T. Tsotsis, "A Catalytic/Sorption Hybrid Process for Landfill Gas Cleanup." Industrial & Engineering Chemistry Research (1997), 36(10), 4100-4107.

Extended European Search Report received in co-pending EP Appl. No. 14759823.9, dated Jun. 20, 2016 (12 pages).

Li et al., "High-Capacity Sulfur Dioxide Absorbents for Diesel Emissions Control," Ind. Eng. Chem. Res., 2005, vol. 44, No. 1, pp. 168-177.

Li et al., "Synthesis and Characterization of Silver Hollandite and Its Application in Emission Control," Chem. Mater. vol. 17, No. 17, 2005, pp. 4335-4343.

Office Action received in co-pending JP Appl 2015-561477 dated Sep. 5, 2016, with English translation (6 pages).

\* cited by examiner

FUEL CELL SYSTEM HAVING BIOGAS DESULFURIZER ASSEMBLY WITH MANGANESE OXIDE DESULFURIZER MATERIAL

This invention relates to fuel cells and, in particular, to desulfurization of fuel using manganese oxide containing materials in fuel cell systems.

A fuel cell is a device which directly converts chemical energy stored in hydrocarbon fuel into electrical energy by means of an electrochemical reaction. Generally, a fuel cell comprises an anode and a cathode separated by an electrolyte, which serves to conduct electrically charged ions. Molten carbonate fuel cells operate by passing a reactant fuel gas through the anode, while oxidizing gas is passed through the cathode. In order to produce a useful power level, a number of individual fuel cells are stacked in series with an electrically conductive separator plate between each cell.

Current fuel cell technology requires clean fuel gas composed of hydrogen or a mixture of hydrogen and carbon monoxide, which can be generated from hydrocarbon-containing feedstocks, such as natural gas, propane, anaerobic digester gas, petroleum-based liquids or coal, through a reforming process. Most hydrocarbon-containing feedstocks contain sulfur, which causes reforming and anode catalyst poisoning and is known to significantly diminish the performance of fuel cell anodes and reforming catalysts. Therefore, prior to the reforming process, sulfur and sulfur-containing compounds have to be removed from the fuel gas to a part per billion level before the fuel gas enters the fuel cell.

In addition to the commonly used hydrocarbon-containing feedstocks, biogas produced from waste water treatment, agricultural waste, food processing waste, landfill gases, and the like, has the potential to replace a significant amount (10-15%) of current natural gas applications in North America. Due to high efficiency and low emission of $CO_2$ and NOx, use of biogas for power generation is environmentally friendly. However, different biogases typically include impurities, including $H_2S$, siloxanes and organic sulfur compounds, which limit biogas applications, and particularly limit the uses of biogas in fuel cell applications which have stringent requirements with respect to impurities. Current technologies for biogas clean-up include $H_2S$ and siloxane removal from the biogas for internal combustion engines or microturbines, but do not include removal of small organic sulfur compounds required for fuel cell applications. Conditioning technologies and media typically used for natural gas in fuel cell applications are not suitable for use with biogas because of high moisture content in biogas.

Moreover, in some cases, natural gas and methane gas from coal-bed sources contain high moisture levels and may also contain sulfur compounds that are difficult to remove. Similar to biogas, conventional conditioning technologies and media are not suitable for use with natural gas and methane saturated with water and containing difficult to remove sulfur compounds.

For typical fuel cell applications using biogas, dual fuel option or blending dry natural gas with biogas has been employed in cases of insufficient process gas production or production interruption. However, such dual fuel or blending options require a separate natural gas cleanup and processing system, which requires additional space and costs.

SUMMARY OF THE INVENTION

The object of the present invention is to provide a desulfurizing material and system that is capable of effectively removing organic sulfur compounds from a fuel gas regardless of moisture content and impurities present in the fuel gas. Another object of the present invention is to provide a desulfurizer system which is fuel flexible so that it is capable of processing different types of fuels with different types and concentrations of sulfur compounds and so that it allows for combining dry fuel gas cleanup processing together with wet gas cleanup processing.

These and other objects of the invention are realized in a desulfurizer material for desulfurizing fuel supplied to a fuel cell system, the desulfurizer material comprising one or more manganese oxide materials having an octahedral molecular sieve (OMS) structure. The desulfurizer material is resistant to moisture and is capable of removing organic sulfur containing compounds and $H_2S$. The OMS structure of the manganese oxide material is one of OMS-1 and OMS-2, wherein OMS-1 has a 3×3 tunnel structure and a tunnel size of about 6.9 Å and OMS-2 has a 2×2 tunnel structure and a tunnel size of about 4.6 Å. The manganese oxide material has mixed valence and Mn in the OMS structure of the manganese oxide material has an oxidation state between +3 and +4. In some embodiments, the manganese oxide material is doped with one or more doping metals inserted into tunnels of the OMS structure. The amount of the one or more doping metals is between 0 and 50% of a total metal content of the desulfurizer material, and the one or more doping metals comprise one or more of transition metals, alkali metals and alkali earth metals. For example, the doped manganese oxide material is one of Cu-OMS-2, CoOMS-2 and Fe-OMS-2. In some embodiments, the manganese oxide material is doped with a first doping metal in the amount of 0 to 50% of the total metal content of the desulfurizer material and with a second doping metal in the amount of 0 to 25% of the total metal content of the desulfurizer material.

A desulfurizer assembly for desulfurizing fuel for use in a fuel cell system and which includes one or more desulfurizer beds is also disclosed. At least one of the one or more desulfurizer beds comprises the above-described desulfurizer material. In certain embodiments, the desulfurizer assembly comprises a plurality of desulfurizer beds, including a first desulfurizer bed and a second desulfurizer bed. The first desulfurizer bed and the second desulfurizer bed comprising either same desulfurizer material or different desulfurizer materials.

A fuel cell system that includes a fuel cell stack including an anode side and a cathode side and the desulfurizer assembly as described above is also disclosed. In some embodiments, the fuel cell system includes a fuel cleanup assembly for cleanup fuel before the fuel is conveyed to the desulfurizer assembly, the fuel cleanup assembly comprising one or more of an $H_2S$ removal unit for removing $H_2S$ from the fuel, a moisture conditioning unit for removing moisture from the fuel and a siloxane removal unit for removing siloxanes from the fuel. In certain embodiments, the fuel cell system also includes a heating assembly for at least one of pre-heating a biogas digester that provides biogas fuel to the fuel cleanup assembly and pre-heating desulfurized fuel output from the desulfurizer assembly. The heating assembly pre-heats the fuel using one of anode exhaust and cathode exhaust, and the heating assembly is further configured to receive water and to humidify the desulfurized fuel with the received water.

To provide fuel flexibility, the fuel cell system in some embodiments is configured to operate on two or more fuels of different composition. In such embodiments, the fuel cell system further comprises a first fuel supply assembly for supplying a first fuel to the fuel cleanup assembly, and a second fuel supply assembly for supplying a second fuel, having a different composition from the first fuel, to the desulfurizer assembly, wherein the second fuel is not conveyed through the fuel cleanup assembly. In this fuel cell system, a heating assembly is provided for preheating the biogas digester that provides the first fuel to the fuel cleanup assembly. In some embodiments, the fuel cell system further comprises a control assembly for controlling at least one of: (a) flow rates of first fuel and second fuel through the first and second supply assemblies, respectively, and (b) flow of first fuel and second fuel through the one or more desulfurizer beds in the desulfurizer assembly. In certain embodiments, the fuel cell system is a molten carbonate fuel cell system, while in other embodiments the fuel cell system is a PEM, SOFC or other type of fuel cell system.

A desulfurizing method for desulfurizing one or more fuels for use in a fuel cell system is also described. In the desulfurizing method, the removal of the sulfur-containing compounds is performed by one of an oxidation process and a catalytic oxidative desulfurization process.

BRIEF DESCRIPTION OF THE DRAWINGS

The above and other features and aspects of the present invention will become more apparent upon reading the following detailed description in conjunction with the accompanying drawings, in which.

DETAILED DESCRIPTION

The present invention is directed to desulfurizing materials for removal of sulfur-containing compounds from a variety of fuel gases and suitable for use with both wet and dry fuel gases. The present invention is also directed to fuel cell systems which include a fuel polishing and desulfurizing assemblies capable of polishing and desulfurizing fuels with high water content and capable of processing dual fuels, including a dry fuel and a wet fuel, without requiring a separate fuel processing train.

Figure 1:
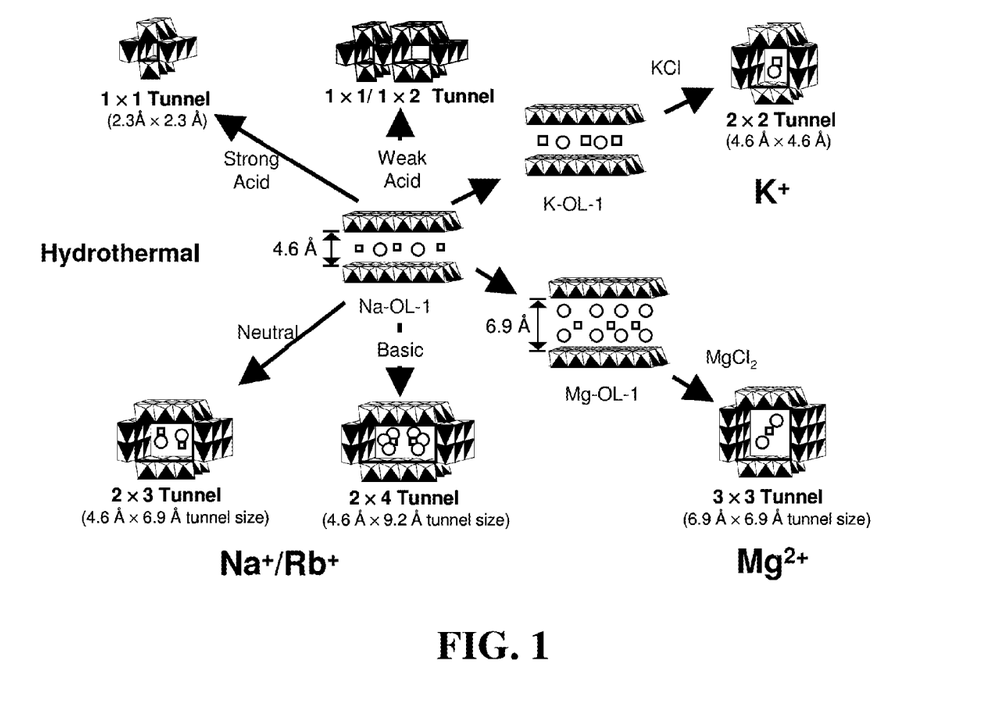
FIG. 1 shows various structures of OMS materials.

In accordance with the present invention, the desulfurizing materials comprise octahedral molecular sieves (OMS), and in particular undoped and doped manganese oxide containing materials with OMS structure. The oxidation state of the Mn in the OMS structures is typically between +3 and +4. FIG. 1 shows different types of OMS structures, with tunnel size of the OMS materials being controlled by a structure director, such as $Na^+/Rb^+$, $K^+$ and $Mg^{2+}$. In the present invention, the manganese oxide OMS desulfurizing material is one of OMS-1 with a tunnel size of about 6.9 Å and a 3×3 tunnel structure, and OMS-2 with a tunnel size of about 4.6 Å and a 2×2 tunnel structure. Alternatively, the manganese desulfurizing materials have an amorphous structure, with the Mn oxidation state being between +3 and +4.

Manganese oxide OMS desulfurizer materials have mixed covalent properties, high surface area and high stability which differentiate manganese oxide OMS materials from $MnO_2$ and permanganates. The mixed valence of the manganese oxide OMS desulfurizer materials provides an excellent mechanism for oxidation-reduction and an ion-exchange capability which allows for modification of the properties of these materials. In addition, the manganese oxide OMS desulfurizer materials are resistant to moisture in the fuel being desulfurized so that they are capable of desulfurizing fuel with or without moisture present therein.

As mentioned above, the manganese oxide OMS desulfurizer materials may be undoped or doped. In certain embodiments, the manganese oxide OMS desulfurizer materials are doped by using one or more transition metals in the framework of the crystal structures or by inserting transition metal or non-transition metal ions into the tunnels of the OMS structure by ion-exchange. For example, most cations, such as Fe, Cu, Ag, Mg, and Co, etc. may be used as the doping materials for doping the manganese oxide OMS desulfurizer materials. The doping transition metals generally improve the sulfur capacity of the manganese oxide OMS desulfurizer materials, and can be added in amounts of 0-50% (mole) of the total metal content of the desulfurizer materials. Illustrative examples of doped manganese oxide OMS desulfurizer materials include, but are not limited to Cu-OMS-2, Co-OMS-2 and Fe-OMS-2. In other embodiments, multiple metal species may be used for doping the manganese oxide OMS desulfurizer materials, including transition metals, alkali, and alkali earth metals. For example, two different metals may be used to dope the manganese oxide desulfurizer materials, including at least one of a transition metal, an alkali metal and an alkali earth metal, with the amount of the first doping metal being about 0-50% (mole) of the total metal content and the amount of the second doping metal being about 0-25% (mole) of the total metal content of the desulfurizer materials. Illustrative examples of manganese oxide OMS desulfurizer materials doped with two or more metals include, but are not limited to, manganese oxide OMS materials doped with K, Mg, Fe, Co, Ag, Cu, Zn, Ni and mixtures thereof.

The manganese oxide OMS desulfurizer materials of the present invention are used to remove sulfur from a variety of fuels, including natural gas, biogas, such as anaerobic digester gas (ADG), and other types of fuel. Moisture resistance of the manganese oxide OMS desulfurizer materials allows them to be used for desulfurizing fuels having high moisture content, as well as fuels with low moisture content. Generally, the manganese oxide OMS desulfurizer materials remove sulfur-containing compounds from the fuel through oxidation and/or catalytic oxidative desulfurization and are effective for organic sulfur compounds and $H_2S$. In addition to being used for desulfurizing different fuels, these manganese oxide OMS desulfurizer materials can be used as polishing media for biogas after bulk $H_2S$ is removed from the biogas.

Figure 2:
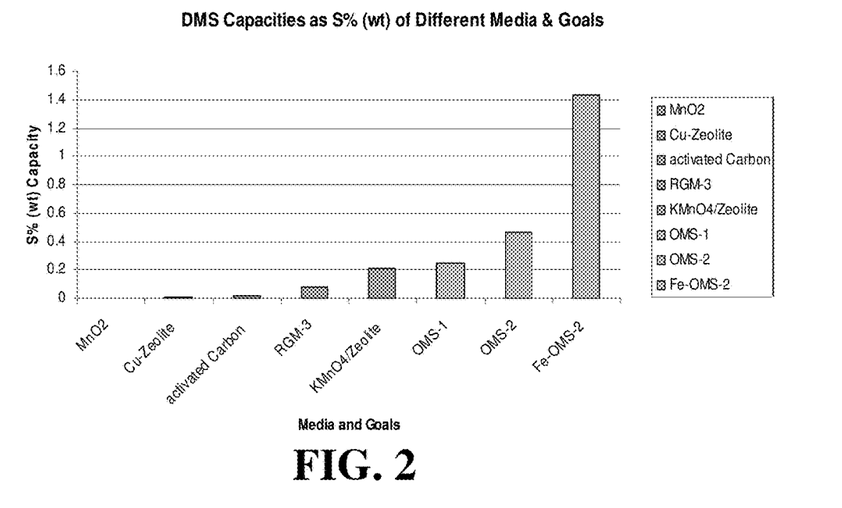
FIG. 2 shows a bar graph comparing DMS capacities of conventional sorbents with DMS capacities of OMS desulfurizer materials of the present invention.

Different doped and undoped OMS desulfurizer materials were tested for their capacity to remove dimethyl sulfide (DMS) from fuel and were compared to various commercially available desulfurizers. The tests were conducted at ambient conditions and the fuel conveyed through the desulfurizer materials being tested included 70% methane and 30% $CO_2$. The water content in the fuel was 3,000 ppm, DMS content in the fuel was 16 ppm and the gas hourly space velocity (GHSV) was 6,600 $h^{-1}$ during all tests. Table 1 summarizes the test results and FIG. 2 shows the comparison of DMS capacities between commercial desulfurizers/sorbents and OMS desulfurizer materials of the present invention. In FIG. 2, the media or sorbents tested are shown on the X-axis while Y-axis represents the DMS capacity (S % wt).

TABLE 1

| Desulfurizer material/sorbent | DMS Capacity (% wt) S |
|---|---|
| $MnO_2$ | 0 |
| Activated Carbon | 0.04 |
| Cu-Activated Carbon | 0.08 |
| Cu-Zeolites | 0.02 |
| 6% $KMnO_4$/Zeolites | 0.21 |
| OMS-1 | 0.24 |
| OMS-2 | 0.46 |
| Cu-OMS-2 | 0.42 |
| Co-OMS-2 | 0.48 |
| Fe-OMS-2 | 1.43 |

As can be seen from FIG. 2 and Table 1, the capacities for DMS removal of OMS-1, OMS-2 and doped OMS-2 desulfurizer materials of the present invention are substantially higher than the DMS capacities of conventionally used sorbents, such as $MnO_2$, activated carbon, Cu-doped activated carbon and doped zeolites. In particular, DMS capacity of Fe-doped manganese oxide OMS-2 desulfurizer material is 6 times the capacity of $KMnO_4$/Zeolites, which is the best conventionally used product. Although the sulfur capacity of the different manganese oxide OMS desulfurizer materials was tested at ambient temperatures, the sulfur capacity of these materials is increased at elevated temperatures. Thus, manganese oxide OMS desulfurizer materials of the present invention may be used in desulfurizers that operate at ambient conditions as well as at elevated temperatures. Moreover, although the capacity of the different manganese oxide OMS desulfurizer materials was tested with respect to DMS, these materials work with similar or higher capacity for removal of other organic sulfur compounds and $H_2S$.

Figure 3:
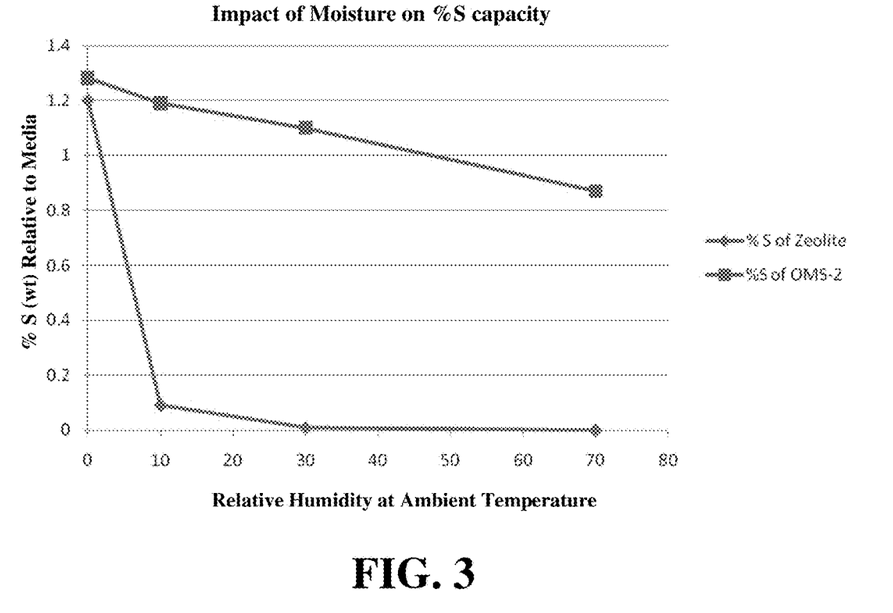
FIG. 3 shows a graph demonstrating impact of moisture content in the fuel to DMS capacity of a conventional zeolite compared to the DMS capacity of OMS-2 desulfurizer materials.
Figure 4:
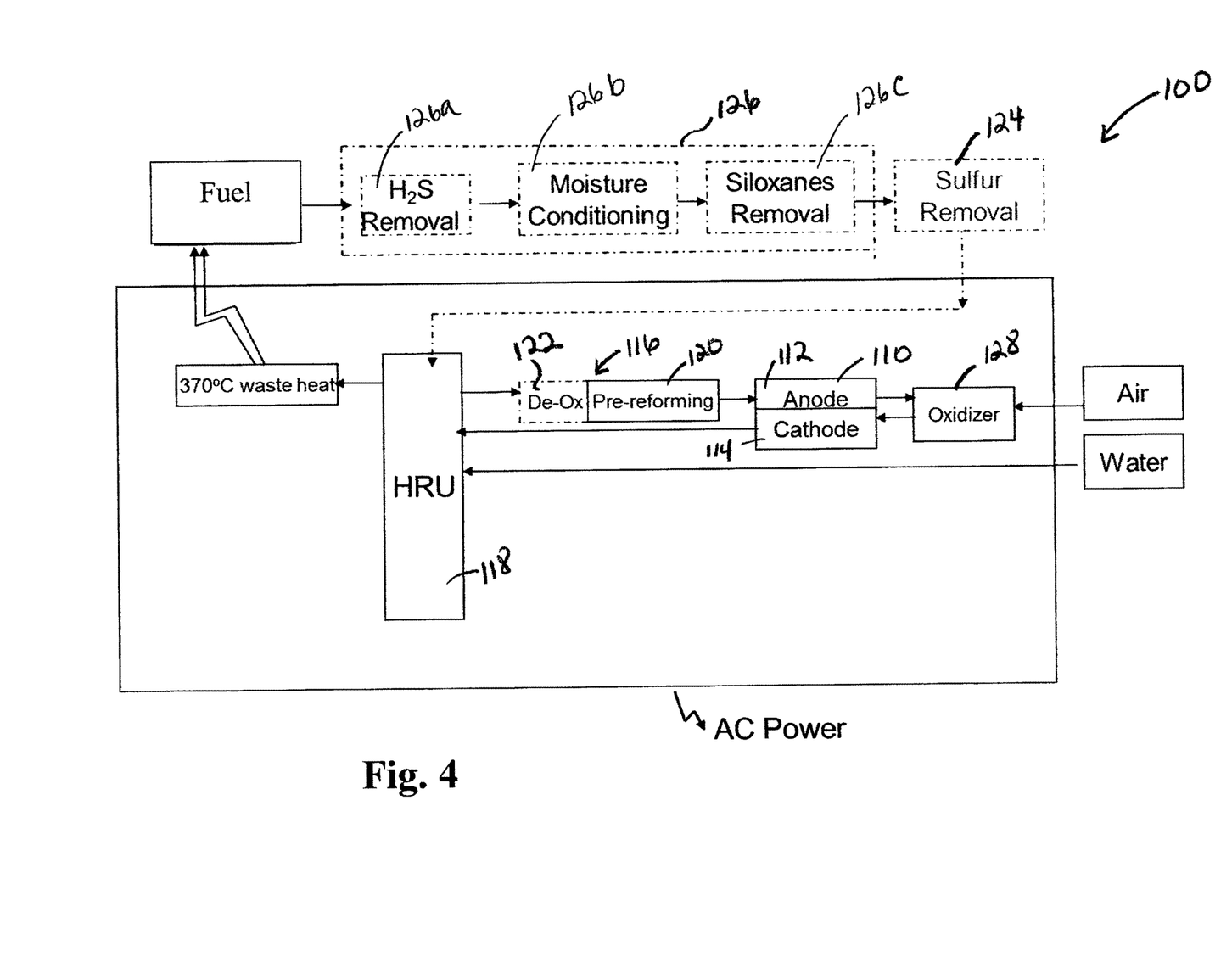
FIG. 4 shows a fuel cell system employing biogas processing.
Figure 5:
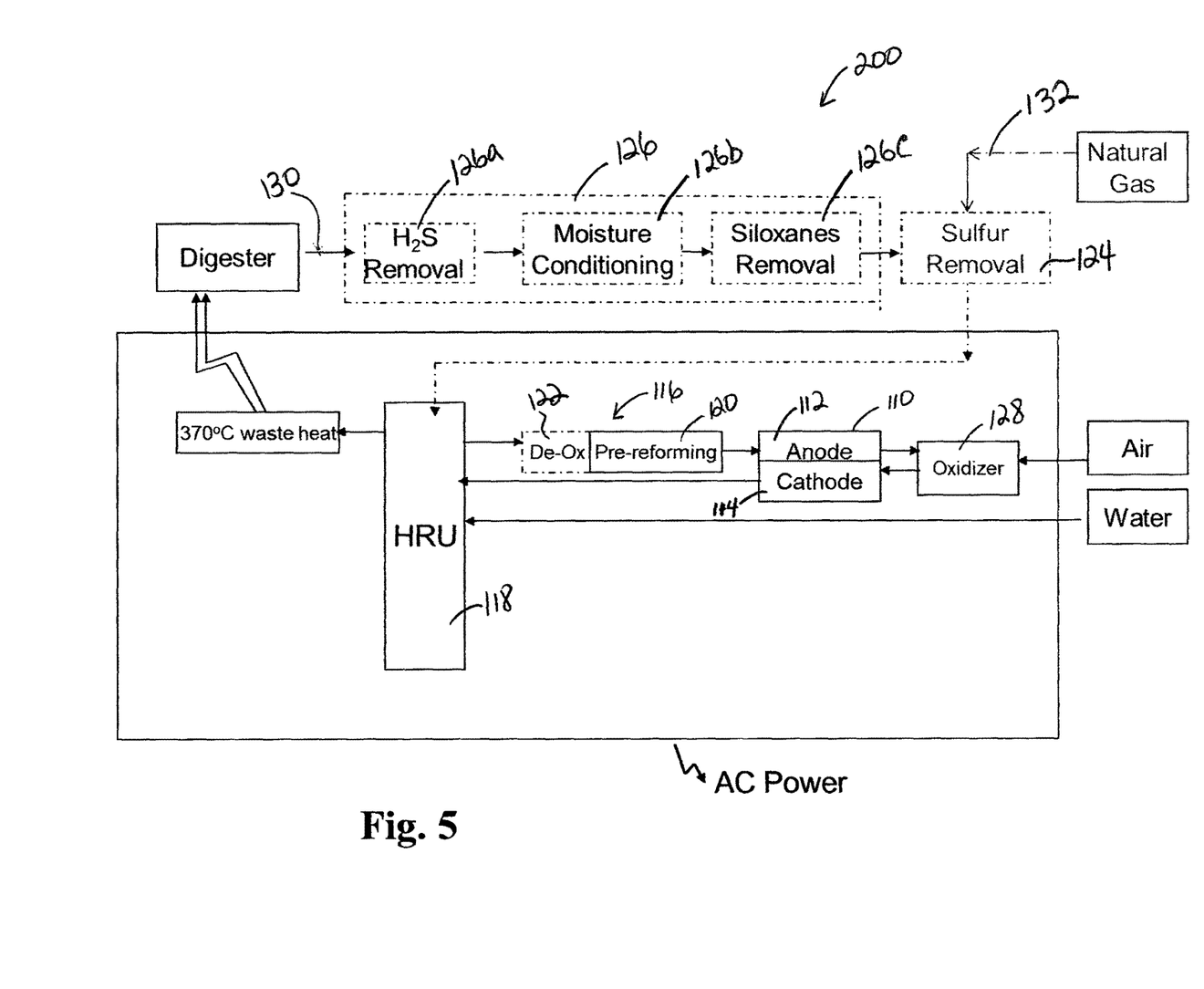
FIG. 5 shows a fuel cell system with fuel flexible cleanup for use with biogas and natural gas.

In addition to higher capacity, manganese oxide OMS desulfurizer materials have substantially higher moisture resistance than the conventionally used products. Almost all of the conventionally used products were seriously affected by moisture, including Cu-Zeolite which is the best DMS sorbent for use with natural gas. In contrast, Fe-doped OMS-2 material was only slightly affected by the moisture content in the fuel, thus providing the moisture resistance required for desulfurizing biogas. FIG. 3 is a graph showing the impact of moisture in the fuel on the sulfur-capacity of a conventional zeolite and of the manganese oxide OMS-2 desulfurizer material. In FIG. 3, the X-axis represent the relative humidity of the fuel at ambient temperature, while Y-axis represent the sulfur capacity of the desulfurizer material. As can be seen in FIG. 3, as the relative humidity of the fuel increases, the sulfur removal capacity of the conventional zeolite substantially decreases. For example, the sulfur removal capacity of the conventional zeolite used to desulfurize dry gas (moisture content <200 ppm) is about 1.2% S (wt), while its sulfur removal capacity decreases to about 0.1 at the relative humidity of 10% and further decreases to almost 0 as the relative humidity increases to 30% and above. In contrast, the sulfur removal capacity of the OMS-2 material was only slightly affected by the increased moisture in the fuel, decreasing from 1.4% S (wt) when desulfurizing dry gas to about 0.9% S (wt) at the relative humidity of 70. As mentioned above, the substantially higher moisture resistance of the manganese oxide OMS desulfurizer materials allows them to be used for desulfurizing fuels with high moisture content, such as humidified natural gas and biogas fuels, and to be used with dual-fuel systems. FIGS. 4 and 5 show fuel cell systems which use the manganese oxide OMS desulfurizer materials for desulfurizing natural gas and/or biogas fuels.

FIG. 4 shows a fuel cell system employing biogas processing, which may also be used with other fuels including dry natural gas, humidified natural gas, and other fuels. As shown in FIG. 4, the fuel cell system 100 includes a fuel cell 110, typically in a form of a fuel cell stack with an anode side 112 and a cathode side 114, a heat recovery unit/humidifier assembly 118, a pre-processing assembly 116, including a pre-reforming unit 120 and in some embodiments, a deoxidizing unit 122, a biogas bulky cleanup assembly 126 and a fuel desulfurizer (polishing) assembly 124. The fuel cell system of FIG. 4 also includes an oxidizer assembly 128 for oxidizing anode exhaust with air and outputting oxidizing gas to the cathode side 114 of the fuel cell 110.

As shown in FIG. 4, the fuel cell system 100 is supplied with fuel gas (such as biogas/ADG gas), which in this illustrative embodiment is provided from a biogas digester to the biogas bulky cleanup assembly 126. In the biogas digester, organic material is digested by enzymes to produce and output methane biogas fuel. In order to achieve a good biogas production, the temperature in the digester needs to be maintained at 37-40° C., and thus, the digester requires heat in order to maintain this temperature. Waste heat from the fuel cell exhaust can be used for providing the heat needed by the biogas digester, as shown in the illustrative embodiment of FIG. 4. Waste heat at 370° C. is suitable for maintaining the temperature in the digester at optimal levels.

It is understood that other fuels, such as other biogas fuels, wet and/or dry natural gas, coal-bed methane, etc., may be used by the fuel cell system 100, and that in certain embodiments, the biogas bulky cleanup assembly 126 may be omitted or bypassed by the fuel, depending on the needs for the particular fuel gas. In addition, depending on the fuel used by the system 100, another suitable fuel supply may be used instead of the biogas digester to provide the fuel to the bulky cleanup assembly, and/or the desulfurizer. Waste heat from the fuel cell may be provided, if needed, to preheat the fuel before supplying the fuel to the bulky cleanup assembly 126 or to the desulfurizer 124.

The illustrative biogas bulky cleanup assembly 126 shown in FIG. 4 includes an $H_2S$ desulfurizing unit 126a for removing $H_2S$ from the biogas fuel, a moisture conditioning unit 126b for removing at least a portion of the moisture from the biogas fuel and a siloxane removal unit 126c for removing siloxanes from the biogas fuel. The $H_2S$ desulfurizing unit 126a includes a desulfurizing material for removing $H_2S$ from the fuel when the biogas fuel is conveyed therethrough. The desulfurizing material in the $H_2S$ desulfurizing unit is preferably resistant to the moisture in the biogas fuel and may include, but is not limited to, one or more of Iron sponge, Sulfatreat, or any media that can remove $H_2S$ from the biogas fuel. The moisture conditioning unit 126b includes compression and chiller to remove moisture from the biogas. The siloxane removal unit 126c includes media such as activated carbon, silica gel, or zeolites. In some embodiments, the manganese oxide OMS materials of the present invention may be used as polishing media following biogas cleanup assembly 126.

After the biogas fuel is cleaned by the biogas cleanup assembly 126, the biogas fuel is conveyed to the desulfurizer (polishing) assembly 124 of the present invention for removal of sulfur-containing compounds from the biogas.

The desulfurizer assembly 124 includes at least one desulfurizing bed comprising the manganese oxide OMS desulfurizer material described above. In some embodiments, the desulfurizer assembly may include two or more desulfurizing beds, with each of the beds having the same or different manganese oxide OMS desulfurizer materials. In addition, in some embodiments with two or more desulfurizing beds, at least one of the beds includes manganese oxide OMS desulfurizer materials, while another one or more of the beds may include other OMS or non-OMS materials. The at least one desulfurizing bed of the desulfurizer assembly 124 is disposed in a housing, and in the embodiments of the desulfurizer assembly including multiple desulfurizing beds, each bed may be disposed in a separate housing, or two or more beds may be disposed in series in a common housing. In other embodiments, the desulfurizer assembly 124 may be arranged as a lead-lag desulfurizer assembly having multiple desulfurizing beds and switching between the operational and standby desulfurizing beds. An exemplary lead lag desulfurizer assembly construction is disclosed in U.S. Pat. No. 7,063,732, assigned to the same assignee herein. As discussed above, the manganese oxide OMS desulfurizer material removes sulfur-containing compounds from the fuel, including organic sulfur-containing compounds and $H_2S$, and is resistant to moisture present in the fuel.

After desulfurization in the desulfurizer assembly 124, the desulfurized biogas fuel is conveyed through the heat recovery unit 118 where it is pre-heated using waste heat from cathode exhaust and/or oxidizer. The heat recovery unit 118 also functions as a humidifier and receives water for humidifying the desulfurized biogas fuel. Pre-heated and humidified biogas fuel is then conveyed to the pre-processing assembly 116 in which the biogas fuel may be de-oxidized in the de-oxidizer 122 to remove oxygen in the biogas and at least partially reformed in a pre-reforming unit 120. The biogas fuel is thereafter conveyed to the anode side 112 of the fuel cell 110.

As shown in FIG. 4, anode exhaust is burned with air in the oxidizer 128, which outputs heated oxidant gas to the cathode side 114 of the fuel cell 110. Cathode exhaust is then provided to the heat recovery unit 118 to recover waste heat from the cathode exhaust and the waste heat can be used to heat the biogas digester.

The system shown in FIG. 4 provides the necessary processing for the digester fuel and biogas fuel using the biogas cleanup assembly 126 and the desulfurizing assembly 124 so as to provide fuel suitable for use in the fuel cell 110. Although the biogas cleanup assembly 126 and the desulfurizing assembly 124 are described as being used to process biogas fuel, these assemblies may be used with other fuels, as needed. Another example of a fuel cell system 200 is shown in FIG. 5, which is modified to allow fuel flexible processing for a variety of fuels, including digester gas, biofuels, natural gas, etc. The system 200 shown in FIG. 5 includes similar components to those of the system of FIG. 4.

As shown in FIG. 5, the fuel cell system 200 includes a fuel cell 110, usually in a form of a fuel cell stack with an anode side 112 and a cathode side 114, a heat recovery unit/humidifier assembly 118, a pre-processing assembly 116, including a pre-reforming unit 120 and in some embodiments, a deoxidizing unit 122, a desulfurizer assembly 124 and a biogas bulky cleanup assembly 126. The fuel cell system of FIG. 5 also includes an oxidizer assembly 128 for oxidizing anode exhaust with air and outputting oxidizing gas to the cathode side 114 of the fuel cell 110. In FIG. 5, the construction and arrangement of these components is similar to FIG. 4, and thus, similar reference numbers are used for these components and a detailed description thereof will be omitted.

As shown in FIG. 5, the fuel cell system 200 is adapted to be supplied with a first fuel (e.g., biogas) through a first input assembly 130 and the biogas bulky cleanup assembly 126. The first fuel may be a digester fuel gas (ADG), other biogas fuel, blended fuels, coal-bed methane fuel or other fuel requiring fuel polishing. As discussed above, biogas fuel may be supplied to the biogas bulky cleanup assembly 126 from a biogas digester, and waste heat from the fuel cell exhaust may be used for heating the digester so as to maintain temperatures in the digester at optimal levels for methane production. In addition, if the first fuel needs to be preheated, then waste heat from the fuel cell exhaust may be used to preheat the first fuel before the it is conveyed to the biogas bulky cleanup assembly 126 and/or the desulfurizer assembly 124. In the embodiment shown and as in the system of FIG. 4, the waste heat from cathode exhaust fuel leaving the heat recovery unit 118 is used to heat the biogas digester.

As in the system of FIG. 4, the illustrative biogas bulky cleanup assembly 126 in FIG. 5 includes a $H_2S$ desulfurizing unit 126a for removing $H_2S$ from the first fuel, a moisture conditioning unit 126b for removing at least a portion of the moisture from the first fuel and a siloxane removal unit 126c for removing siloxanes from the first fuel. After the first fuel is cleaned in the biogas bulky cleanup assembly 126, the first fuel is conveyed to the desulfurizer assembly 124 of the present invention for removal of sulfur-containing compounds from the first fuel. As discussed above, the desulfurizer assembly 124 includes at least one desulfurizing bed comprising the manganese oxide OMS desulfurizer material described above, and in some embodiments, the desulfurizer assembly may include two or more desulfurizing beds having the same or different desulfurizer materials. As also described above, the manganese oxide OMS desulfurizer material may be doped or undoped.

As shown in FIG. 5, the system is adapted to receive a second fuel through a second input assembly 132 and to convey the second fuel to the desulfurizer assembly 124, without conveying the second fuel to the biogas cleanup assembly 126. The second fuel may be different from the first fuel and may be wet or dry natural gas or any other fuel that does not require siloxane removal before being desulfurized. In the embodiment shown in FIG. 5, the second input assembly 132 is separate from the first input assembly 130 and provides the second fuel directly to the desulfurizer assembly 124. However, in other embodiments, the second input assembly 132 may be in the form of a bypass assembly around the biogas cleanup assembly 126, wherein the second fuel is provided through the first input assembly 130 and is conveyed to the second input assembly 132 to bypass the second fuel around the biogas cleanup assembly 126 and to provide the second fuel directly to the desulfurizer assembly 124.

In the embodiment shown in FIG. 5, the first and second fuels can be supplied to the fuel cell system 200 separately depending on the fuel requirements of the fuel cell system, or simultaneously, wherein the first fuel undergoes cleanup in the biogas cleanup assembly and the second fuel does not undergo cleanup in the biogas cleanup assembly prior to being desulfurized in the desulfurizer assembly 124. In some embodiments, the supply of the first and second fuels through the first and second input assemblies, respectively, is controlled so as to control the respective amounts or flow rates of the first and second fuels through the respective first and second input assemblies in order to achieve a desired blended or unblended fuel composition. A control assembly (not shown), including a fuel flow control members, such as flow control valves, in the respective first and second input assemblies and a controller for controlling the fuel flow control members, is employed for controlling the supply of the first and second fuels through the respective first and second input assemblies. The controller controls the fuel flow control members based on a variety of factors, including the fuel composition needs of the fuel cell system, fuel availability, load on the fuel cell system, fuel amount requirements of the system, the desulfurizer capacity and operation, and other factors.

Referring again to FIG. 5, the desufurizer assembly 124 receives the first and/or the second fuel from the respective first and/or second input assembly and removes sulfur-containing compounds from the fuel(s). As discussed herein above, the desulfurizer assembly 124 includes one or more desulfurizer beds. In some embodiments, both the first fuel and the second fuel are desulfurized in the same desulfurizer bed(s) either simultaneously or separately. However, in other embodiments, the desulfurizer assembly 124 includes one or more first desulfurizer beds and one or more second desulfurizer beds, and the one or more first desulfurizer beds are used for desulfurizing the first fuel only while one or more second desulfurizer beds are used for desulfurizing the second fuel. In such embodiments, the desulfurizer used in the one or more first desulfurizer beds may be either the same or different from the desulfurizer used in the one or more second desulfurizer beds. This construction allows the desulfurizer beds to be optimized for the type and composition of the fuel being desulfurized by the desulfurizer assembly. In yet other embodiments, the desulfurizer assembly includes a plurality of desulfurizer beds with the same or different desulfurizers, and the flows of the first and second fuels through the desulfurizer assembly are controlled so that each of the first and second fuels is conveyed through an appropriate desulfurizer bed(s) of the desulfurizer assembly for optimal desulfurization conditions. This control may be accomplished based on a variety of factors, including the respective compositions of the first and second fuels, the respective flow rates of the first and second fuels, the respective compositions of the desulfurizer beds, etc. A desulfurizer control assembly, which is part of the above control assembly or separate therefrom, may be used for controlling the flow of first and second fuels through the desulfurizer bed(s). Such desulfurizer control assembly includes a plurality of flow control members for controlling the flow of the first and second fuels through the appropriate desulfurizer beds and a controller, which may be a separate controller from the above-described controller or may be implemented in the above-described controller, for controlling the flow control members.

After desulfurization in the desulfurizer assembly 124, the desulfurized fuel, including desulfurized first fuel and/or desulfurized second fuel, is conveyed through the heat recovery unit 118 where it is pre-heated using waste heat from cathode exhaust and/or oxidizer. The heat recovery unit 118 also functions as a humidifier and receives water for humidifying the desulfurized fuel. Pre-heated and humidified fuel is then conveyed to the pre-processing assembly 116 in which the fuel may be de-oxidized in the de-oxidizer 122 and at least partially reformed in a pre-reforming unit 120. The fuel is thereafter conveyed to the anode side 112 of the fuel cell 110.

The above described system of FIG. 5 can be used with systems operating on dual fuels, such as one dry fuel gas and one moist fuel gas. For example, the system of FIG. 5 may be used with systems operating on pipeline dry natural gas and wet biogas. In this way, the system of FIG. 5 provides flexibility in the type of fuel used for generating electrical power, regardless of the sulfur compound content, moisture content and other impurities content of the fuel.

In all cases it is understood that the above-described arrangements are merely illustrative of the many possible specific embodiments which represent applications of the present invention. Numerous and varied other arrangements can be readily devised in accordance with the principles of the present invention without departing from the spirit and the scope of the invention.

We claim:

1. A fuel cell system comprising:
   a biogas fuel supply assembly;
   a desulfurizer assembly configured to receive biogas fuel from the biogas fuel supply assembly and to desulfurize the biogas fuel, the desulfurizer assembly comprising one or more desulfurizer beds; and
   a fuel cell stack including an anode side and a cathode side, the anode side of the fuel cell stack receiving the desulfurized biogas fuel from the desulfurizer assembly;
   wherein each of the one or more desulfurizer beds comprises a desulfurizer material configured to desulfurize biogas fuel conveyed through said one or more desulfurizer beds, and
   wherein the desulfurizer material in at least one of the one or more desulfurizer beds comprises a manganese oxide material that has an octahedral molecular sieve (OMS) structure and is doped with Fe,
   wherein the manganese oxide material comprises OMS-2 having a 2×2 tunnel structure, and
   wherein an amount of the Fe in the desulfurizer material is greater than 0% (mole) and less than 50% (mole) of a total metal content of the desulfurizer material.

2. The fuel cell system in accordance with claim 1, wherein:
   the desulfurizer assembly comprises a plurality of desulfurizer beds, including a first desulfurizer bed and a second desulfurizer bed, and
   the first desulfurizer bed and the second desulfurizer bed comprises different desulfurizer materials.

3. The fuel cell system in accordance with claim 1, further comprising a cleanup assembly configured to process the biogas fuel before the biogas fuel is conveyed to the fuel cell assembly, the cleanup assembly comprising an $H_2S$ removal unit for removing $H_2S$ from the biogas fuel.

4. The fuel cell system in accordance with claim 3, wherein:
   the biogas fuel supply comprises a biogas digester; and
   the fuel cell system further comprises a heating assembly configured to heat the biogas digester using waste heat from the fuel cell stack.

5. The fuel cell system in accordance with claim 4, wherein the heating assembly is configured to pre-heat the desulfurized fuel using one of anode exhaust and cathode exhaust, and the heating assembly is further configured to receive water and to humidify the desulfurized fuel with the received water.

6. The fuel cell system in accordance with claim 3, wherein the fuel cell system is configured to operate on two or more fuels of different compositions and the fuel cell system further comprises:

a second fuel supply assembly for supplying a second fuel, having a different composition from the first fuel, to the desulfurizer assembly,
wherein the second fuel is not conveyed through the cleanup assembly.

7. The fuel cell system in accordance with claim 6, wherein the biogas fuel supply assembly comprises a biogas digester and the fuel cell system further comprises a heating assembly configured to heat the biogas digester so as to maintain the temperature in the biogas digester at a predetermined temperature.

8. The fuel cell system according to claim 6, further comprising a control assembly for controlling at least one of:
   (a) flow rates of first fuel and second fuel through the biogas fuel supply assembly and the second supply assembly, respectively; and
   (b) flow of the biogas fuel and the second fuel through the one or more desulfurizer beds in the desulfurizer assembly.

9. The fuel cell system in accordance with claim 3, wherein the cleanup assembly further comprises a moisture conditioning unit for removing moisture from the biogas fuel.

10. The fuel cell system in accordance with claim 9, wherein the cleanup assembly further comprises a siloxane removal unit for removing siloxanes from the biogas fuel.

11. The fuel cell system in accordance with claim 6, wherein the second fuel is natural gas.

12. The fuel cell system in accordance with claim 1, wherein the manganese oxide material of the desulfurizer material in said at least one of the one or more desulfurizer beds is further doped with a second doping metal selected from the group consisting of K, Mg, Co, Ag, Cu, Zn, Ni, and mixtures thereof.

13. The fuel cell system in accordance with claim 1, wherein the manganese oxide material is resistant to moisture and capable of removing organic sulfur containing compounds and $H_2S$.

14. The fuel cell system in accordance with claim 1, wherein the OMS-2 has a tunnel size of about 4.6 Å.

15. The fuel cell system in accordance with claim 1, wherein the biogas fuel supply assembly is configured to supply biogas fuel having a relative humidity of at least 10% to the desulfurizer assembly.

16. The fuel cell system in accordance with claim 1, wherein the biogas fuel supply assembly is configured to supply biogas fuel having a relative humidity of at least 30% to the desulfurizer assembly.

* * * * *